(12) United States Patent
Matsuoka et al.

(10) Patent No.: US 8,481,608 B2
(45) Date of Patent: Jul. 9, 2013

(54) SILICONE MONOMER

(75) Inventors: Yosuke Matsuoka, Tsukuba (JP);
Nobuyuki Yoshioka, Tsukuba (JP);
Nobuyuki Sakamoto, Tsukuba (JP);
Toshiya Itei, Tsukuba (JP); Ryota Kobayashi, Tsukuba (JP); Mao Sorimachi, Tsukuba (JP)

(73) Assignee: NOF Corporation, Tokyo (JP)

( * ) Notice: Subject to any disclaimer, the term of this patent is extended or adjusted under 35 U.S.C. 154(b) by 178 days.

(21) Appl. No.: 13/145,062

(22) PCT Filed: Jan. 19, 2010

(86) PCT No.: PCT/JP2010/050533
§ 371 (c)(1),
(2), (4) Date: Jul. 18, 2011

(87) PCT Pub. No.: WO2010/082659
PCT Pub. Date: Jul. 22, 2010

(65) Prior Publication Data
US 2011/0282008 A1    Nov. 17, 2011

(30) Foreign Application Priority Data
Jan. 19, 2009 (JP) ................ 2009-009202

(51) Int. Cl.
*G02B 1/04* (2006.01)
(52) U.S. Cl.
USPC .......... 523/107; 526/279; 556/436; 556/437; 556/438; 556/439; 556/440; 556/442
(58) Field of Classification Search
None
See application file for complete search history.

(56) References Cited

U.S. PATENT DOCUMENTS

| | | |
|---|---|---|
| 3,808,178 A | 4/1974 | Gaylord |
| 4,139,548 A | 2/1979 | Tanaka et al. |
| 4,139,692 A | 2/1979 | Tanaka et al. |
| 4,235,985 A | 11/1980 | Tanaka et al. |
| 2009/0299022 A1 | 12/2009 | Ichinohe |

FOREIGN PATENT DOCUMENTS

| | | | |
|---|---|---|---|
| JP | 54-055455 A | | 5/1979 |
| JP | 54-061126 A | | 5/1979 |
| JP | 55-015110 A | | 2/1980 |
| JP | 56-022325 A | | 3/1981 |
| JP | 10-265532 | * | 10/1998 |
| JP | 11-310613 A | | 11/1999 |
| JP | 2001-002732 A | | 1/2001 |
| JP | 2008-202060 A | | 9/2008 |
| WO | WO 02/051951 | * | 7/2002 |
| WO | 2009/121148 A | | 10/2009 |
| WO | 2010/024372 A1 | | 3/2010 |

OTHER PUBLICATIONS

Atarashii Ganka, "Pure Vision®," 2007, vol. 24, No. 6, p. 732.
Tadatomi Nishikubo, "Addition Reaction of Epoxy Compounds with Esters and Its Application for Polymer Syntheses," Journal of Synthetic Organic Chemistry, 1991, vol. 49, No. 3, pp. 218-233.

* cited by examiner

*Primary Examiner* — Marc Zimmer
(74) *Attorney, Agent, or Firm* — Sughrue Mion, PLLC

(57) ABSTRACT

The invention provides a silicone monomer having high purity and suitable for use in the manufacture of ophthalmic devices, and a contact lens produced from the silicone monomer as a polymerizable component. The silicone monomer is represented by the formula (1):

$$CH_2=C(R)-C(=O)-O-CH_2-CH(OC(=O)-CH_2-CH_2-C(=O)-O-(CH_2)_n-Si(Y^1)(O-Si(Y^2)(Y^3)(Y^4))_a(O-Si(Y^5)(Y^6)(Y^7))_b-O-Si(Y^8)(Y^9))$$ (1)

wherein $Y^1$ to $Y^9$ each independently stands for an alkyl group having 1 to 4 carbon atoms, n is an integer of 0 to 3, a and b each independently denotes an integer of 0 or 1, and R stands for a hydrogen atom or a methyl group.

5 Claims, 2 Drawing Sheets

SILICONE MONOMER

CROSS REFERENCE TO RELATED APPLICATIONS

This application is a National Stage of International Application No. PCT/JP2010/050533, filed Jan. 19, 2010, which claims priority from Japanese Patent Application No. 2009-009202, filed Jan. 19, 2009, the contents of all of which are incorporated herein by reference in their entirety.

FIELD OF ART

The present invention relates to silicone monomers for use in manufacture of ophthalmic devices, such as contact lenses, intraocular lenses, and keratoprosthesis. The silicone monomers of the present invention provide polymers of high transparency and oxygen permeability and suitable for application in the eyes, so that they are particularly suitable as monomers for contact lenses.

BACKGROUND ART

Silicone compounds such as TRIS and SiGMA represented by the formulae below are conventionally known as device monomers for contact lenses.

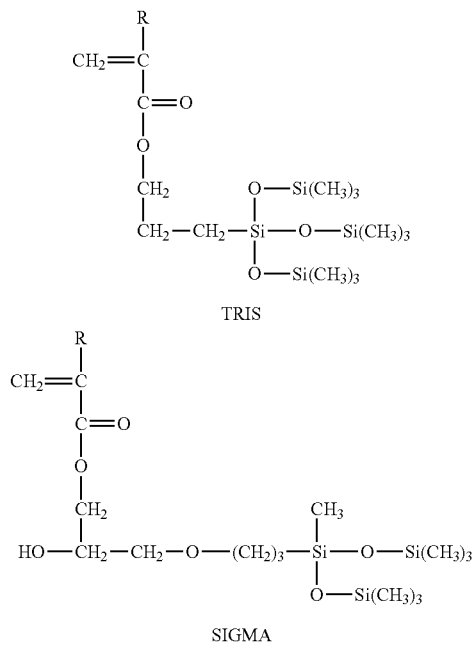

TRIS

SIGMA

TRIS stands for 3-[tris(trimethylsiloxy)silyl]propyl methacrylate, which is a monomer classically known as a material for intraocular lenses (Patent Publication 1). However, TRIS is inferior in compatibility with hydrophilic monomers, such as 2-hydroxyethyl methacrylate (HEMA), and when copolymerized with such hydrophilic monomers, will not provide transparent monomers, and cannot be used as a lens material.

It is also known that combination of TRIS with other hydrophilic monomers often results in strongly water-repellent surfaces in a hydrous state, and thus inconvenient for use as a soft contact lens material (Non-patent Publication 1).

In the attempt of overcoming these drawbacks, SiGMA mentioned above, i.e. methyl bis(trimethylsiloxy)silyl propyl glycerol methacrylate, has been developed and used as a compatibilizing monomer for silicone hydrogel contact lenses (Patent Publications 2 and 3).

SiGMA also acts as an oxygen permeability agent for its moderate oxygen permeability. SiGMA is a monomer formed by addition reaction of methacrylic acid and epoxy silicone, and exhibits good hydrophilicity due to formation of hydroxyl groups upon compounding. However, reaction of carboxylic acid and an epoxy group produces isomers (Non-patent Publication 2 and Patent Publication 4), which have similar properties, and are hard to be separated and purified for use through ordinary methods. It is also known that, after formation of SiGMA, carboxylic acid is further added to the hydroxyl group in the glycerin portion of SiGMA to form by-products, which may adversely affect lens properties.

On the other hand, there are proposed high-purity monomers produced by reaction of a methacrylic halide and straight chain polyether-modified silicone (Patent Publication 5). These polyether derivatives, when they have two or more repeats of a constitutional unit, generally contain trimers and tetramers as by-products, which requires column separation and purification or precision distillation for fractionation, and only monomers of which ether is of a single structure, may be obtained conveniently. Thus it has been hard to produce hydrophilic monomer structures in an industrial scale by the reaction of a methacrylic halide and straight chain polyether-modified silicone.

In view of the above, in the art of ophthalmic monomers, silicone monomers are demanded which have improved oxygen permeability, hydrophilicity, and high purity, and which are applicable to inexpensive uses such as daily disposable contact lenses, and convenient to manufacture.

PRIOR ART PUBLICATIONS

Patent Publications

Patent Publication 1: U.S. Pat. No. 3,808,178-A

Patent Publication 2: JP-54-61126-A

Patent Publication 3: JP-11-310613-A

Patent Publication 4: JP-2001-2732-A

Patent Publication 5: JP-2008-202060-A

Non-Patent Publications

Non-Patent Publication 1: Atarashii Ganka, Vol. 24(6), 2007, p 732

Non-Patent Publication 2: Journal of Synthetic Organic Chemistry, Japan, Vol. 49(3), 1991, p 219

SUMMARY OF THE INVENTION

It is an object of the present invention to provide a silicone monomer which is hydrophilic, excellently oxygen permeable, does not or hardly contain isomers or by-products, is useful in the art of ophthalmic monomers, applicable to inexpensive uses such as daily disposable contact lenses, and easy to manufacture.

The present inventors have carried out molecular design of silicone monomers which are suitable as ophthalmic monomers, and newly found out hydrophilic silicone monomers, to thereby complete the present invention.

According to the present invention, there is provided a silicone monomer represented by the formula (1):

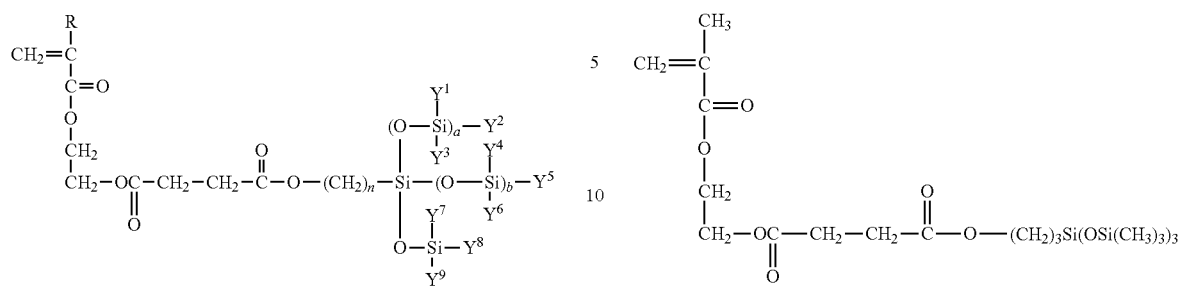

(1)

wherein $Y^1$ to $Y^9$ each independently stands for an alkyl group having 1 to 4 carbon atoms, n is an integer of 0 to 3, a and b each independently denotes an integer of 0 or 1, and R stands for a hydrogen atom or a methyl group.

According to the present invention, there is also provided a contact lens obtained by polymerizing a polymerizable component comprising the above-mentioned silicone monomer.

EFFECT OF THE INVENTION

The silicone monomer of the present invention, which is easy to manufacture, may be obtained easily in high purity, and provides a colorless, transparent polymer when copolymerized with a polymerizable monomer such as a (meth) acrylic monomer, even when it is in a hydrous state. Thus the silicone monomer of the present invention may be used as a high purity ophthalmic monomer which is suitable for the art of ophthalmic devices wherein little isomers and by-products are desired, and is optimal as a contact lens material.

PREFERRED EMBODIMENTS OF THE INVENTION

Figure 1:
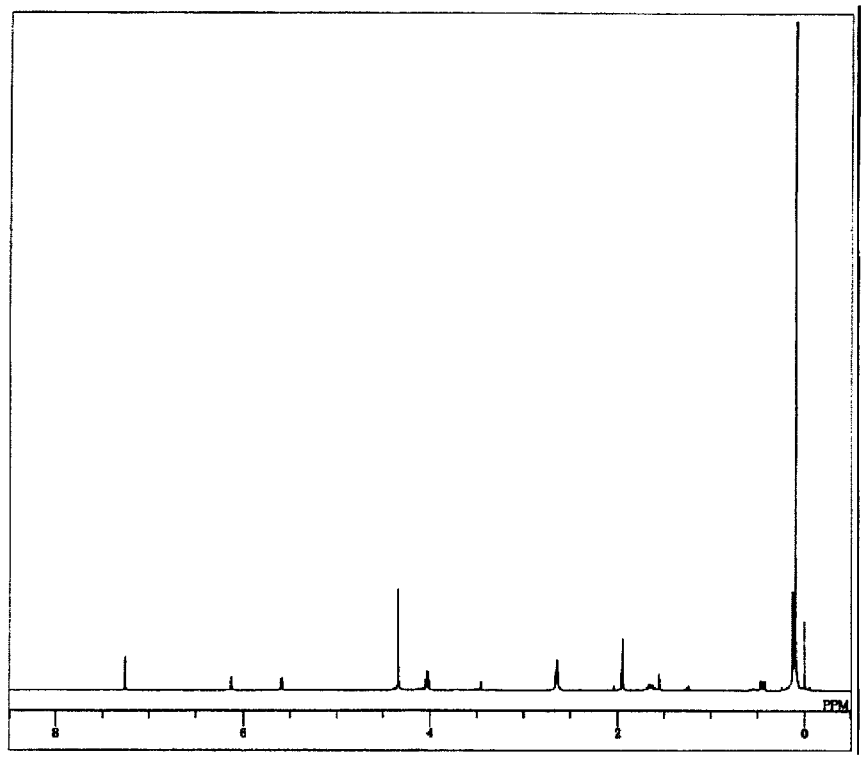
FIG. 1 is a chart showing the $^1$H-NMR spectrum of the monomer prepared in Example 1.

The present invention will now be explained in detail.

The silicone monomer according to the present invention is represented by the formula (1) mentioned above.

In the formula (1), $Y^1$ to $Y^9$ each independently stands for an alkyl group having 1 to 4 carbon atoms. Examples of an alkyl group having 1 to 4 carbon atoms may include methyl, ethyl, n-propyl, 2-propyl, n-butyl, and t-butyl groups. Represented by n is an integer of 0 to 3, and each independently represented by a and b is an integer of 0 or 1. R stands for a hydrogen atom or a methyl group.

A monomer represented by the formula (1) wherein R is a methyl group, $Y^1$ to $Y^9$ are all methyl groups, and a and b are 1, is specifically represented by the formula (2) below. This monomer is particularly preferred as an ophthalmic monomer with improved oxygen permeability.

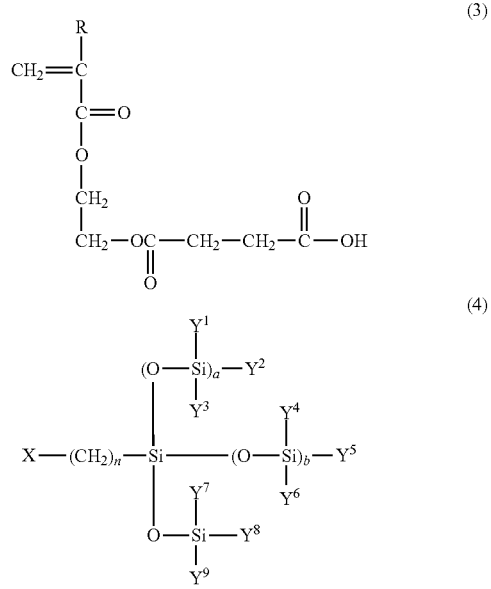

The silicone monomer represented by the formula (1) according to the present invention may be obtained by applying known synthesis methods, such as the following method.

Specifically, the present silicone monomer may be obtained by reacting 2-(meth)acryloyloxyethyl succinic acid represented by the formula (3) and a silicone compound represented by the formula (4):

In the formula (3), R stands for a hydrogen atom or a methyl group. In the formula (4), X stands for a halogen, such as Cl, Br, or I, preferably Br or I. $Y^1$ to $Y^9$ each independently stands for an alkyl group having 1 to 4 carbon atoms. Represented by n is an integer of 0 to 3. Each independently represented by a and b is an integer of 0 or 1.

The reaction may be carried out, for example, by reacting 2-(meth) acryloyloxyethyl succinic acid represented by the formula (3) and a silicone compound represented by the formula (4) in the presence of an organic solvent.

For the reaction, the charging amounts of the 2-(meth) acryloyloxyethyl succinic acid represented by the formula (3) and a silicone compound represented by the formula (4) are usually 10 to 80:20 to 90, preferably 50 to 75:25 to 50 in molar ratio.

The organic solvent may preferably be, for example, N,N-dimethylformamide, dimethylsulfoxide, and acetonitrile, and most preferably N,N-dimethylformamide for its reactivity and solvent price.

The amount of the organic solvent to be used is usually 2 to 10 times more by mass than the total amount of the above monomers.

The reaction preferably proceeds with a base group present in the reaction system, since acid is produced as the reaction proceeds. Examples of such a base group may include potassium carbonate, sodium carbonate, sodium hydroxide, potassium hydroxide, triethlyamine, and diazabicyclo undecene (DBU). For a high yield, potassium carbonate and triethylamine are preferred.

The amount of the base group, if any, is usually 1 to 3 moles, preferably 1 to 2 moles, based on 1 mole of the silicone compound represented by the formula (4).

The reaction may be carried out, for example, in a constant-temperature facility usually at 20 to 100° C., preferably 40 to 80° C. At a temperature lower than 20° C., the reaction temperature may be disadvantageously long, whereas at a temperature over 100° C., a side reaction of decomposition may occur. The reaction time is usually 2 to 20 hours.

More specific embodiment of the reaction may be, for example, to add 2-(meth)acryloyloxyethyl succinic acid represented by the formula (3) to an organic solvent, to which the above-mentioned base group is optionally added, and, for example, within 3 hours, preferably within 1 hour, the silicone compound represented by the formula (4) is gradually added to react.

The silicone compound represented by the formula (4), which is used as a starting material in the above-mentioned reaction, is preferably a high-purity product since its purity affects that of the resulting silicone monomer. Incidentally, a high-purity commercial product may not necessarily be used as the silicone compound of the formula (4), and those synthesized according to the techniques known from JP-2004-307348-A, JP-2004-352677-A, and the like may be used instead. In the latter case, the silicone compound may preferably be highly purified in advance through known extraction or distillation methods.

The silicone monomer represented by the formula (1) according to the present invention may be used as a material for polymerization in various applications. The most preferably the present silicone monomer may be used as a polymerizable component for contact lenses.

The contact lens according to the present invention includes a polymer obtained by polymerizing a polymerizing component containing the silicone monomer of the formula (1) into the shape of a contact lens.

The polymerizable component may solely be the silicone monomer of the formula (1), but usually contains other monomers optionally that are polymerizable with the silicone monomer of the formula (1). The ratio of the silicone monomer of the formula (1) to such other monomers is usually 1:9 to 8:2 by mass.

The above-mentioned other monomers as a polymerizable component may suitably be selected from the monomers that are usually used as lens monomers. For example, for enhancing the surface hydrophilicity of a contact lens, preferably used as said other monomers are water-soluble monomers, such as (meth)acrylic acid, itaconic acid, crotonic acid, cinnamic acid, vinyl benzoic acid, phosphorylcholine (meth)acrylate, polyalkylene glycol mono(meth)acrylate, polyalkylene glycol monoalkyl ether (meth)acrylate, 2-hydroxyethyl (meth)acrylate, 2,3-dihydroxypropyl(meth)acrylate, glycerol (meth)acrylate, N-vinylformamide, N-vinylacetamide, and N-methyl-N-vinylacetamide. Among these, 2-hydroxyethyl(meth)acrylate is particularly preferably used for enhancing the surface hydrophilicity.

For the purpose of controlling the flexibility of contact lenses, preferably used as said other monomers contained in the polymerizable component aside from the water-soluble monomer may be, for example, polyalkylene glycol bis (meth)acrylate, trimethylolpropane tris(meth)acrylate, pentaerythritol tetrakis(meth)acrylate, N,N-dimethylacrylamide, N,N-diethylacrylamide, N,N-di-n-propylacrylamide, N,N-diisopropylacrylamide, N,N-di-n-butylacrylamide, N-acryloyl morpholine, N-acryloyl piperidine, N-acryloyl pyrrolidine, N-methyl(meth)acrylamide, N-vinylpyrrolidone, N-vinylcaprolactam, N-vinyloxazolidone, 1-vinylimidazole, N-vinylcarbazole, vinylpyridine, and vinylpyrazine.

For improving the shape-retainability of contact lenses, preferably used as said other monomers contained in the polymerizable component aside from the water-soluble monomer may be, for example, alkyl(meth)acrylates, such as methyl(meth)acrylate and ethyl(meth)acrylate; polyfunctional (meth)acrylates, such as siloxane macromer having a carbon-carbon unsaturated bond at both ends; halogenated alkyl(meth)acrylates, such as trifluoroethyl(meth)acrylate and hexafluoroisopropyl(meth)acrylate; aromatic vinyl monomers, such as styrene, α-methylstyrene, and vinylpyridine; and vinylesters, such as vinylacetate.

Further, as other components, hydrophobic monomers may be used as required, such as 3-[tris(trimethylsiloxy)silyl]propyl(meth)acrylate, 3-[bis(trimethylsiloxy)methylsilyl]propyl(meth)acrylate, 3-[(trimethylsiloxy)dimethylsilyl]propyl(meth)acrylate, 3-[tris(trimethylsiloxy)silyl]propyl (meth)acrylamide, 3-[bis(trimethylsiloxy)methylsilyl]propyl(meth)acrylamide, 3-[(trimethylsiloxy)dimethylsilyl]propyl(meth)acrylamide, [tris(trimethylsiloxy)silyl]methyl (meth)acrylate, [bis(trimethylsiloxy)methylsilyl]methyl (meth)acrylate, [(trimethylsiloxy)dimethylsilyl]methyl (meth)acrylate, [tris(trimethylsiloxy)silyl]methyl(meth) acrylamide, [bis(trimethylsiloxy)methylsilyl]methyl(meth) acrylamide, [(trimethylsiloxy)dimethylsilyl]methyl(meth) acrylamide, [tris(trimethylsiloxy)silyl]styrene, [bis(trimethylsiloxy)methylsilyl]styrene, [(trimethylsiloxy)dimethylsilyl]styrene, N-[3-[tris(trimethylsiloxy)silyl]propyl]vinyl carbamate, N-[3-[bis(trimethylsiloxy)methylsilyl]propyl]vinyl carbamate, and N-[3-[(trimethylsiloxy)dimethylsilyl]propyl]vinyl carbamate.

Among the other polymerizable monomers mentioned above, water-soluble monomers are most preferably used in producing the contact lenses of the present invention.

Upon polymerization of the polymerizable components to be used for the contact lenses of the present invention, a thermal polymerization initiator, such as peroxides and azo compounds, or a photopolymerization initiator may be added as required for ready polymerization.

For thermal polymerization, an initiator having optimal decomposition characteristics at desired reaction temperatures may suitably be selected for use. That is, peroxides or azo compounds having a 10-hour half-life temperature of 40 to 120° C. are preferred.

The photopolymerization initiator may be, for example, a carbonyl compound, a sulfur compound, a halogen compound, or a metal salt.

These polymerization initiators may be used alone or in mixture, and preferably at 0.5 to 2 parts by mass based on 100 parts by mass of the polymerizable components.

The contact lens according to the present invention may be obtained by polymerizing the polymerizable components into the shape of a contact lens according to a know method.

EXAMPLES

The present invention will now be explained in more detail with reference to Examples and Comparative Examples, which are not intended to limit the present invention.

Example 1

Synthesis of MASS (methacryloyloxyethyl succinate 3-[tris(trimethylsiloxy)silyl]propyl)

A 1 L pear-shaped flask was charged with 59.39 g of 2-methacryloyloxyethyl succinate (0.258 moles, manufactured by KYOEISHA CHEMICAL CO., LTD.), 637.56 g of N,N-dimethylformamide, 29.74 g potassium carbonate (0.215 moles), and 4-methoxyphenol, and the resulting solution was heated to 40° C. After the temperature was raised, 100.0 g of 3-iodopropyltris(trimethylsiloxy)silane (0.215 moles) was added dropwise, and the mixture was further stirred for 2 hours. The reaction solution was cooled, and then transferred to a 5 L separating funnel, diluted with 1200 g of ethyl acetate, washed three times with 1200 g of 5% sodium hydrogen carbonate, and further washed twice with 1200 g of 2% sodium sulfate. By removing the solvent, 112.9 g of a colorless, transparent silicone compound of the formula below was obtained (at 75.5% yield).

The purity of the obtained silicone compound was 91.1 mass %. The conditions for the purity determination of the silicone monomer (GC method) were as follows:
Gas Chromatograph: GC system 7890A manufactured by AGILENT
Detector: FID, 250° C.
Capillary Column: HP-1 (0.53 mm 30 m 2.65 μm) manufactured by J&W
Programmed Temperature Rise: 80° C. (0 min)→20° C./min→250° C. (20 min)
Inlet Temperature: 250° C.; Carrier Gas: helium (5 ml/min); Split Ratio: 5:1; Injection amount: 2 μl By the $^1$H-NMR measurement of the obtained silicone compound, peaks derived from $CH_2=C-$ (2H) were observed around 6.1 ppm and 5.6 ppm, a peak derived from the methyl group of methacrylic acid (3H) was observed around 1.95 ppm, a peak derived from $-O-CH_2CH_2-O-$ of methacrylate (4H) was observed around 4.3 ppm, a peak derived from $-O-C(=O)CH_2CH_2C(=O)-O-$ (4H) was observed around 2.65 ppm, peaks derived from $-O-CH_2CH_2CH_2-Si-$ (6H) were observed at 4.0 ppm (2H), 1.6 ppm (2H), and 0.4 ppm (2H), and a peak derived from siloxane (27H) was observed around 0.1 ppm. The $^1$H-NMR measurement was made using JNM-AL400 manufactured by JOEL LTD. and CDCl$_3$ as a solvent. The results of the $^1$H-NMR measurement are shown in FIG. 1.

Figure 2:
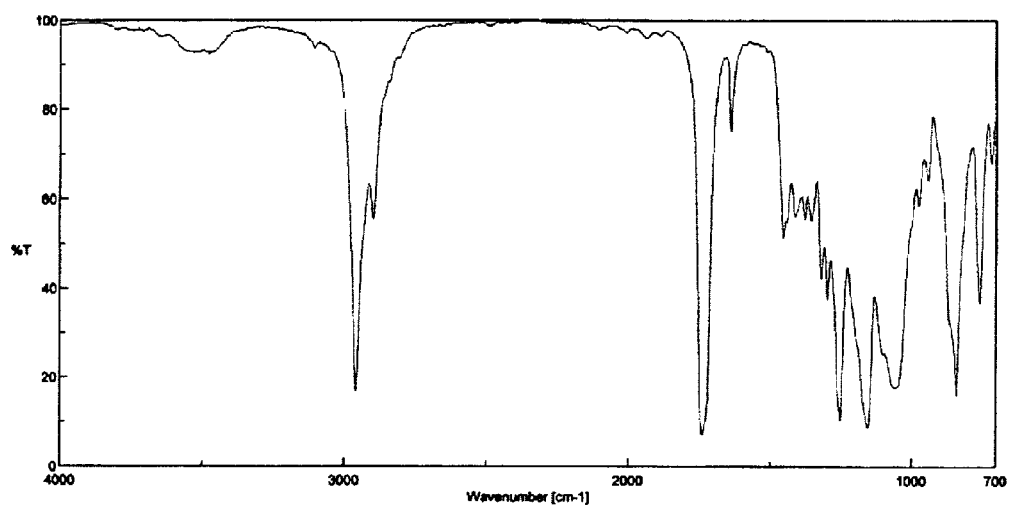
FIG. 2 is a chart showing the IR spectrum of the monomer prepared in Example 1.

By the IR measurement of the obtained silicone compound, a peak derived from a double bond was observed at 1635 cm$^{-1}$, a peak derived from a methacrylate bond and a succinate bond was observed at 1740 cm$^{-1}$, a peak derived from a Si—O—Si bond was observed at 1060 cm$^{-1}$, peaks derived from a methyl or methylene group were observed at 2960 cm$^{-1}$, 1410 cm$^{-1}$, 1300 cm$^{-1}$, and a peak derived from a methyl group bonded to siloxane was observed at 840 cm$^{-1}$. Incidentally, the peak at 1715 cm$^{-1}$ derived from carboxylic acid was not observed. The infrared absorption (IR) measurement was made by a liquid membrane technique, with the cumulated number of sixteen. The results of the IR measurement are shown in FIG. 2.

The structure of the obtained silicone compound was determined by mass measurement (LC-MS method) using LC-MS manufactured by WATERS CORPORATION, with the LC eluent conditions of acetonitrile/50 mM ammonium acetate aqueous solution (9/1) (results not shown).

As a result of the above measurements, the silicone compound obtained in Example 1 was identified as a silicone monomer represented by the formula (2):

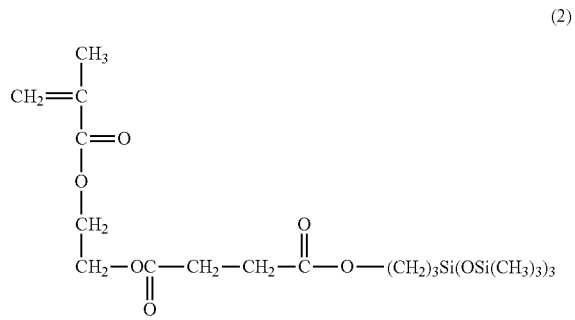

(2)

Example 2

Synthesis of AESS (acryloyloxyethyl succinate 3-[tris(trimethylsiloxy)silyl]propyl)

A 1 L pear-shaped flask was charged with 83.66 g of 2-acryloyloxyethyl succinate (0.387 moles, manufactured by KYOEISHA CHEMICAL CO., LTD.), 1018.32 g of N,N-dimethylformamide, 44.61 g of potassium carbonate (0.323 moles), and 4-methoxyphenol, and the resulting solution was heated to 40° C. After the temperature was raised, 150.0 g of 3-iodopropyltris(trimethylsiloxy)silane (0.323 moles) was added dropwise, and the mixture was further stirred for 2 hours. The reaction solution was cooled, and then transferred to a 5 L separating funnel, diluted with 1200 g of ethyl acetate, washed three times with 1200 g of 5% sodium hydrogen carbonate, and further washed twice with 2% sodium sulfate. By removing the solvent, 134.0 g of a colorless, transparent silicone compound of the formula below was obtained (at 75.0% yield).

Figure 3:
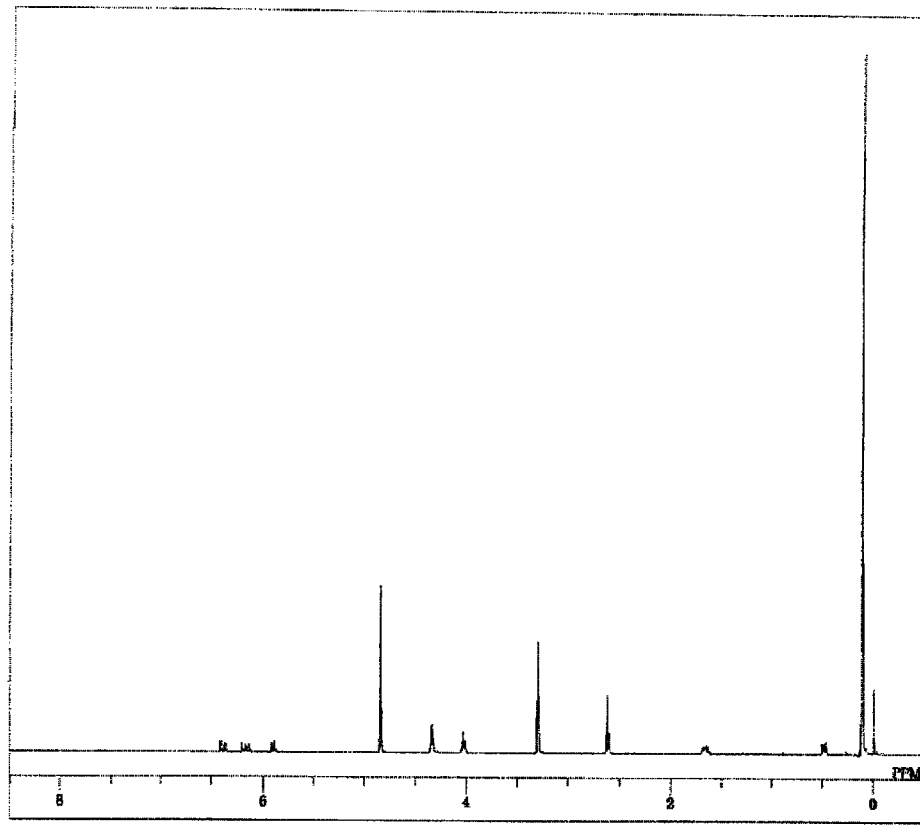
FIG. 3 is a chart showing the $^1$H-NMR spectrum of the monomer prepared in Example 2.

By the $^1$H-NMR measurement of the obtained silicone compound, peaks derived from $CH_2=CH-$ (2H) were observed around 6.40 ppm, 6.16 ppm, and 5.90 ppm, a peak derived from $-O-CH_2CH_2-O-$ of methacrylate (4H) was observed around 4.33 ppm, a peak derived from $-O-C(=O)CH_2CH_2C(=O)-O-$ (4H) was observed around 2.63 ppm, peaks derived from $-O-CH_2CH_2CH_2-Si-$ (6H) were observed at 4.03 ppm (2H), 1.65 ppm (2H), and 0.49 ppm (2H), and a peak derived from siloxane (27H) was observed around 0.1 ppm. The $^1$H-NMR measurement was made using JNM-AL400 manufactured by JOEL LTD. and CDCl$_3$ as a solvent. The results of the $^1$H-NMR measurement are shown in FIG. 3.

Figure 4:
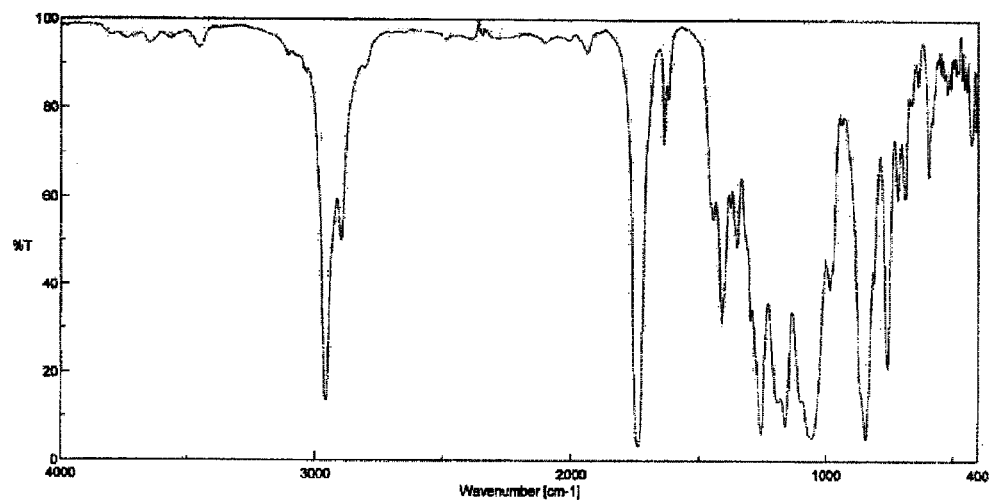
FIG. 4 is a chart showing the IR spectrum of the monomer prepared in Example 2.

By the IR measurement of the obtained silicone compound, a peak derived from a double bond was observed at 1635 cm$^{-1}$, a peak derived from a methacrylate bond and a succinate bond was observed at 1735 cm$^{-1}$, a peak derived from a Si—O—Si bond was observed at 1055 cm$^{-1}$, peaks derived from a methyl or methylene group were observed at 2960 cm$^{-1}$ and 1410 cm$^{-1}$, and a peak derived from a methyl group bonded to siloxane was observed at 840 cm$^{-1}$. Incidentally, the peak at 1715 cm$^{-1}$ derived from carboxylic acid was not observed. The infrared absorption (IR) measurement was made by a liquid membrane technique, with the cumulated number of sixteen. The results of the IR measurement are shown in FIG. 4.

The structure of the obtained silicone compound was determined by mass measurement (LC-MS method) using LC-MS manufactured by WATERS CORPORATION, with the LC eluent conditions of acetonitrile/50 mM ammonium acetate aqueous solution (9/1) (results not shown).

As a result of the above measurements, the silicone compound obtained in Example 2 was identified as a silicone monomer represented by the formula (5):

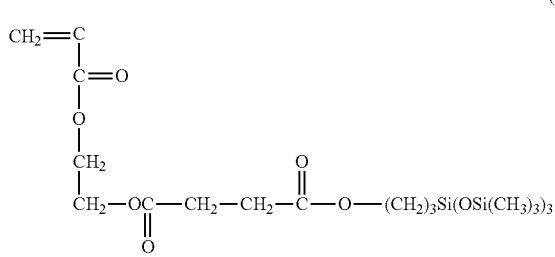

(5)

Example 3

Test on Contact Lens Model Containing Compound of Formula (2) Prepared in Example 1 as Polymerizable Component 40 parts by mass of the compound of formula (2) prepared in Example 1, 60 parts by mass of 2-hydroxyethylmethacrylate, 0.5 parts by mass of ethylene glycol dimethacrylate, and 0.5 parts by mass of azobisisobutyronitrile were mixed and dissolved. The resulting solution was poured into a cell made of a glass plate and a polypropylene plate with a 0.1 mm thick polyethylene terephthalate sheet interposed therebetween as a spacer. The atmosphere in an oven was substituted with nitrogen, and the cell was heated at 100° C. for 2 hours for polymerization. After polymerization, the cured sheet was taken out of the mold, soaked in a 3/1 mixed solution of ethyl alcohol and ion exchanged water for 12 hours, and then in ion exchanged water for 12 hours to obtain a hydrous film. The hydrous film thus obtained was prepared into the shapes required for various measurements, and the transparency (by visual observation), the oxygen permeability, and the surface wettability were evaluated. The oxygen permeability and the surface wettability were evaluated by the following methods. The results are shown in Table 1.

Measurement of Oxygen Permeability Coefficient (DK)

The oxygen permeability coefficient of a circular film sample was measured in water at 25° C. with IPI type film oxygen permeability meter (K-316) manufactured by TSUKUBA RIKA SEIKI CO., LTD.

Evaluation of Surface Hydrophilicity

The surface hydrophilicity was evaluated from the length of the time wherein the water film on the surface of a 1×3 cm² plate-shaped film sample when drawn up from water was retained. The evaluation was made in the following manner. One point or higher was determined as having good water wettability.

Scores: two points for samples which remain wet for 30 seconds or longer after being drawn up; one point for samples which remain wet for not shorter than 3 seconds and less than 30 seconds after being drawn up; and zero point for samples of which water film was drawn off immediately after being drawn up.

Example 4

Test on Contact Lens Model Containing Compound of Formula (2) Prepared in Example 1 as Polymerizable Component A film was prepared in the same way as in Example 2 except that 60 parts by mass of the compound of formula (2) prepared in Example 1, 40 parts by mass of 2-hydroxyethylmethacrylate (HEMA), 0.5 parts by mass of ethylene glycol dimethacrylate (EDMA), and 0.5 parts by mass of azobisisobutyronitrile (AIBN) as a polymerization initiator were mixed, dissolved, and polymerized. The above-mentioned measurements were made, and the results are shown in Table 1.

Comparative Example 1

Test on Contact Lens Model Containing 3-tris(trimethylsilyl)propylmethacrylate (TRIS) as Polymerizable Component A film was prepared in the same way as in Example 3 except that the compound of the formula (2) prepared in Example 1 was replaced with 40 parts by mass of 3-tris (trimethylsilyl)propylmethacrylate (TRIS). The above-mentioned measurements were made, and the results are shown in Table 1.

TABLE 1

|  |  | Ex. 3 | Ex. 4 | Comp. Ex. 1 |
|---|---|---|---|---|
| Composition parts by mass | Compound of Formula (2) | 40 | 60 |  |
|  | TRIS |  |  | 40 |
|  | HEMA | 60 | 40 | 60 |
|  | EDMA | 0.5 | 0.5 | 0.5 |
|  | AIBN | 0.5 | 0.5 | 0.5 |
| Property | Film Transparency | transparent | transparent | white turbid |
|  | Oxygen Permeability (Dk) | 57 | 69 | 60 |
|  | Surface Wettability | 2 | 1 | 0 |

TRIS: 3-tris(trimethylsilyl)propylmethacrylate
HEMA: 2-hydroxyethylmethacrylate
EDMA: ethylene glycol dimethacrylate
AIBN: azobisisobutyronitrile From the results shown in Table 1, it is understood that the contact lens models in Examples 3 and 4 produced with the compound of formula (2) prepared in Example 1 had higher transparency even when the compound was copolymerized with a hydrophilic monomer, 2-hydroxyethylmethacrylate, and retained its oxygen permeability while exhibiting high surface hydrophilicity, compared to contact lens model in Comparative Example 1. Therefore, it was demonstrated that the silicone monomer of the present invention is superior as an ophthalmic monomer, in particular as a contact lens material.

INDUSTRIAL APPLICABILITY

The silicone monomer of the present invention has high purity, and thus is suitably used in the manufacture of ophthalmic devices. The contact lens of the present invention, which is produced from a high purity silicone monomer, has high purity, retains its oxygen permeability while exhibiting high surface hydrophilicity, and applicable to inexpensive uses such as daily disposable contact lenses.

What is claimed is:

1. A silicone monomer represented by the formula (1):

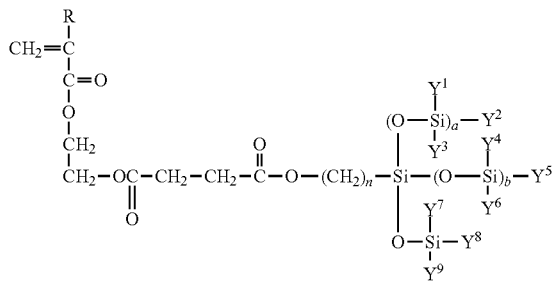

wherein $Y^1$ to $Y^9$ each independently stands for an alkyl group having 1 to 4 carbon atoms, n is an integer of 0 to 3, a and b each independently denotes an integer of 0 or 1, and R stands for a hydrogen atom or a methyl group.

2. A contact lens comprising a polymer obtained by polymerizing a polymerizable component comprising the silicone monomer of claim 1 and other monomer copolymerizable with said silicone monomer.

3. The contact lens according to claim 2, wherein a ratio of said silicone monomer and said other monomer copolymerizable with said silicone monomer is in the range of 1:9 to 8:2 by mass.

4. The contact lens according to claim 2, wherein said other monomer comprises a water-soluble monomer copolymerizable with said silicone monomer.

5. The contact lens according to claim 3, wherein said other monomer comprises a water-soluble monomer copolymerizable with said silicone monomer.

* * * * *